(12) United States Patent
Umezawa et al.

(10) Patent No.: US 8,524,747 B2
(45) Date of Patent: Sep. 3, 2013

(54) PHARMACEUTICAL COMPOSITIONS

(75) Inventors: Kazuo Umezawa, Kanagawa (JP);
Yuichi Ishikawa, Kanagawa (JP);
Shigeru Nishiyama, Kanagawa (JP);
Miyuki Tachibana, Kanagawa (JP);
Ayumi Kaneda, Kanagawa (JP)

(73) Assignee: Keio University, Tokyo (JP)

( * ) Notice: Subject to any disclaimer, the term of this patent is extended or adjusted under 35 U.S.C. 154(b) by 203 days.

(21) Appl. No.: 13/000,442

(22) PCT Filed: Jun. 25, 2009

(86) PCT No.: PCT/JP2009/061636
§ 371 (c)(1),
(2), (4) Date: Mar. 29, 2011

(87) PCT Pub. No.: WO2009/157515
PCT Pub. Date: Dec. 30, 2009

(65) Prior Publication Data
US 2011/0213001 A1 Sep. 1, 2011

(30) Foreign Application Priority Data
Jun. 25, 2008 (JP) .................................. 2008-166290

(51) Int. Cl.
*A61K 31/44* (2006.01)
(52) U.S. Cl.
USPC .......................................... 514/348; 546/296
(58) Field of Classification Search
USPC .......................................... 514/348; 546/296
See application file for complete search history.

(56) References Cited

U.S. PATENT DOCUMENTS 3,435,007 A * 3/1969 Langer et al. ................. 528/322
7,799,782 B2 * 9/2010 Munson et al. ............ 514/234.5

FOREIGN PATENT DOCUMENTS

JP 10-120654 5/1998
WO WO 2007/077861 7/2007

OTHER PUBLICATIONS

Ishikawa et al., "Synthesis and Biological Evaluation on Novel Analogs of 9-Methylstreptimidone, an Inhibitor of NF-κB," *Bioorg. Med. Chem. Lett.* 19(6):1726-1728 (2009).
Saito et al., "Studies on a New Antiviral Antibiotic, 9-Methylstreptimidone. I. Physicochemical and Biological Properties" *The Journal of Antibiotics* 27(3):206-214 (1974).
Singh and Mittal, "Current Status of COX-2 Inhibitors," *Mini-Reviews in Medicinal Chemistry* 8:73-90 (2008).
International Search Report for PCT/JP2009/061636, completed Sep. 8, 2009, mailed Oct. 13, 2009.
English Translation of International Patent Application Publication No. WO2007/077861, published Jul. 12, 2007 (75 pages).
Kobayashi et al., "Action of RANKL and OPG for Osteoclastogenesis," *Critical Reviews in Eukaryotic Gene Expression* 19: 61-72 (2009).

* cited by examiner

*Primary Examiner* — Rei-tsang Shiao
(74) *Attorney, Agent, or Firm* — Clark & Elbing LLP (57) ABSTRACT

The object of the present invention is to provide a pharmaceutical composition that inhibits expression of iNOS and COX-2 without inhibiting NF-κB. The pharmaceutical composition that inhibits expression of iNOS and COX-2 without inhibiting NF-κB contains DTCM glutarimide of the Formula (I) as an effective ingredient, thereby being able to inhibit nitric oxide (NO) production and prostaglandin production.

1 Claim, 11 Drawing Sheets

PHARMACEUTICAL COMPOSITIONS

CROSS-REFERENCE TO RELATED APPLICATIONS

This application is a U.S. National Stage Application of International Patent Application No. PCT/JP2009/061636, filed Jun. 25, 2009, which claims the benefit of Japanese Patent Application Serial No. JP 2008-166290, filed Jun. 25, 2008.

CROSS-REFERENCE TO RELATED APPLICATION

The present application claims the priority based on Japanese Patent Application No. 2008-166290 filed on Jun. 25, 2008, and the disclosure of this parent application is herein incorporated by reference.

TECHNICAL FIELD

The present invention relates to pharmaceutical compositions.

BACKGROUND ART

While nitric oxide (NO) is an essential intrinsic substance engaged in various homeostatic mechanisms, it can also serve as a causal substance of inflammation and the like. NO synthase (NOS) is an enzyme that catalyzes synthesis of NO using L-arginine as substrate and has three isoforms of iNOS, eNOS and nNOS.

iNOS, or inducible NO synthase, does not usually exhibit its enzymatic activity unlike other isoforms. However, upon stimulation of a cell by cytokine, LPS or the like, production of iNOS is induced and large amount of NO are transiently produced. This NO serves as a mediator of inflammation to cause, for example, septic shock, vasodilation due to the inflammation, hypotension, etc.

Similarly, cyclooxygenase 2 (COX-2) is known as an enzyme that is induced by stimulation of cytokines, growth factors etc. This enzyme also functions as a mediator of inflammatory response through production of prostaglandin.

Since these two inducible enzymes participate in major responsive pathways of inflammation, a discovery of a compound to inhibit iNOS and/or COX-2 has been considered to lead to creation of a novel anti-inflammatory agent (Mini Rev Med Chem vol. 8, p. 73-90, 2008).

On the other hand, the expression of iNOS and COX-2 has been known to be induced by activation of the transcription factor NF-κB, particularly in macrophages etc., and thus a development of an anti-inflammatory agent that inhibits expression of iNOS or COX-2 by inhibiting NF-κB has been anticipated.

Further, iNOS is expressed at high level in various tumors such as colon cancer and breast cancer. Since a DTCM glutarimide can inhibit tumoral transformation and metastases of tumor, it is useful as an anti-tumor agent. Proliferation of tumor cells can be suppressed when COX-2 in the tumor cells is inhibited. Because of this fact and other evidence, inhibitors of iNOS and COX-2 are expected also as anti-tumor agents.

However, an agent which inhibits expression of iNOS and COX-2 by inhibiting NF-κB also raises the risk of side effects due to the inhibition of NF-κB.

SUMMARY OF INVENTION

Technical Problem

Accordingly, the present invention was accomplished in order to provide a pharmaceutical composition that can inhibit expression of iNOS and COX-2 without inhibiting NF-κB.

Solution to Problem

The compound according to the present invention is represented by the General Formula (I):

wherein n is an integer of 1 to 24.

Further, the inhibitor of nitric oxide (NO) production, the inhibitor of inducible nitric oxide synthase (iNOS) expression, the inhibitor of prostaglandin production, the suppressor of osteoclast differentiation, the inhibitor of COX-2 expression and the medicament for treating disease mediated by iNOS or COX-2, according to the present invention, contain the abovementioned compound (I) as an effective ingredient. The disease may be an immune disease, a neurodegenerative disease, an inflammatory disease or a tumor.

Further, the method for treating a disease mediated by iNOS or COX-2 according to the present invention includes the step of administering to a patient suffering from the disease a pharmaceutical composition containing the abovementioned compound (I) as an effective ingredient. The disease may be an immune disease, a neurodegenerative disease, an inflammatory disease or a tumor. For example, the disease may be rheumatism, osteoarthritis, collagenosis, Basedow's disease, Parkinson's disease, Alzheimer's disease, multiple sclerosis, amyotrophic lateral sclerosis, infectious disease, arthritis, pyrexia, lumbago, dysmenorrhea, periodontitis, osteoporosis or bone cancer.

DESCRIPTION OF EMBODIMENTS

Embodiments of the present invention are hereinafter described specifically and in detail by referring to Examples, which should not be construed as limiting the present invention thereto.

Unless otherwise explained in the Description of Embodiments or Examples, methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., as well as their modifications/variations are employed. When a commercially available reagent kit or a measuring instrument is used, the protocol attached thereto will be followed unless otherwise explained.

It is to be understood that the object, characteristics, and advantages of the present invention as well as the idea thereof will be apparent to those skilled in the art from the descriptions given herein, and the present invention can be easily reproduced by those skilled in the art based on the descriptions given herein. The embodiments and specific examples of the invention described herein are to be taken as preferred embodiments of the present invention, and these descriptions are presented only for illustrative and/or explanatory purposes and should not be construed as limiting the present invention thereto. It is apparent to those skilled in the art that various modifications may be made based on the descriptions given herein within the intent and scope of the present invention disclosed herein.

==DTCM Glutarimide (DTCM-Glutarimide)==

The compound according to the present invention is a DTCM glutarimide represented by the Formula (I):

(I)

wherein n is, although not particularly limited, preferably an integer of 1 to 24, more preferably an integer of 1 to 18, even more preferably 1 to 12 or 6 to 18, and most preferably 6 to 12.

The DTCM glutarimide may be synthesized, for example, as follows.

First, Compound (II) is dissolved in acetic acid; concentrated sulfuric acid is added to the solution; and the resulting mixture is heated at reflux. Water is added to the reaction mixture, which is then heated at reflux. The mixture is extracted with ethyl acetate, and the resultant organic phase is washed with saturated saline, dried with anhydrous sodium sulfate. And then the solvent is removed under reduced pressure to yield an oily substance. This oily substance is dissolved in dimethyl formamide; 1-(3-dimethyl aminopropyl)-3-ethyl carbodiimide, 4-dimethyl aminopyridine and 1-alkanethiol are added to the solution; and the resulting mixture is stirred at room temperature. Water is then added to the reaction solution thus obtained, which is extracted with chloroform, and the resultant organic phase is washed with saturated saline, and dried with anhydrous sodium sulfate.

After filtration, the solvent is removed by vacuum distillation. The resulting residue is purified by using silica gel column chromatography to yield the Compound (I) as a colorless solid. The number n in the Compound (I) can be adjusted by choosing a certain number of C in the alkane chain of the 1-alkanethiol.

==Inhibitor for iNOS Expression, Inhibitor for COX-2 Expression==

The inhibitor for iNOS expression according to the present invention contains the DTCM glutarimide of the Formula (I) as an effective ingredient, and can inhibit iNOS production by inhibiting iNOS expression without inhibiting NF-κB, resulting in inhibition of nitric oxide (NO) production.

The COX-2 inhibitor according to the present invention contains the DTCM glutarimide of the Formula (I) as an effective ingredient, and can inhibit COX-2 production by inhibiting COX-2 expression without inhibiting NF-κB, resulting in inhibition of prostaglandin production as well as suppression of osteoclast differentiation.

==Medicament for Treating Diseases Mediated by iNOS or COX-2==

The suppression of iNOS production and COX-2 production can lead to treatment of diseases mediated by iNOS and COX-2 respectively. Accordingly, the DTCM glutarimide of the Formula (I), which is capable of suppressing iNOS expression and/or COX-2 expression, is useful for medicament for treating disease mediated by iNOS or COX-2.

The diseases mediated by iNOS or COX-2 as mentioned herein includes, for example, rheumatism such as articular rheumatism, immune diseases including autoimmune diseases such as osteoarthritis, collagenosis and Basedow's disease, neurodegenerative diseases such as Parkinson's disease, Alzheimer's disease, multiple sclerosis and amyotrophic lateral sclerosis, various inflammatory diseases such as infectious diseases, arthritis, pyrexia, lumbago and dysmenorrhea, tumors such as breast cancer, prostate cancer, colon cancer, large bowel cancer, stomach cancer, esophageal cancer, pulmonary cancer, hepatic cancer, pancreatic cancer, squamous cell cancer, brain tumor, bone cancer and multiple myeloma. Further, by inhibiting prostaglandin production, inhibition of neovascularization as well as suppression of inflammation can be made possible; and by suppressing the osteoclast differentiation, treatment of periodontitis, osteoporosis, bone cancer etc., as well as suppression of progression of myeloma, can be made possible. Accordingly, the DTCM glutarimide of the Formula (I) is useful, in particular, for an agent against immune disease, an agent against neurodegenerative disease, an inhibitor of neovascularization, a nonsteroidal anti-inflammatory agent, an antipyretic analgesics, an anti-tumor agent and the like.

==Method for Manufacturing and Administering Agent==

These agents may contain, in addition to the DTCM glutarimide, any of various pharmaceutical ingredients such as pharmaceutically acceptable ordinary carriers, binders, stabilizers, excipients, diluents, pH buffers, disintegrators, solubilizers, solubilizing aids and isotonizers. These agents may be administered to a patient, in a dosage appropriate for sex, body weight, symptom etc. of the patient, and by an appropriate administration route such as oral administration or parenteral administration.

EXAMPLES

(1) Synthesis of DTCM Glutarimide

First, the DTCM glutarimide C-6 represented by the Formula (III) above was synthesized as follows.

One gram of the Compound (II) was dissolved in 10 mL of acetic acid; 1 mL of concentrated sulfuric acid was added to the solution; and the resulting mixture was heated at reflux for 2 hours. 5 mL of water was added to the reaction mixture, which is then heated at reflux for 2 hours. The reaction mixture was extract with ethyl acetate, and the resultant organic phase was washed with saturated saline, dried with anhydrous sodium sulfate, and the solvent was removed under reduced pressure to yield 0.85 g of an oily substance. This oily substance was dissolve in 20 mL of dimethyl formamide; 1.1 g of 1-(3-dimethyl aminopropyl)-3-ethyl carbodiimide, 7.1 g of 4-dimethyl aminopyridine and 1.4 mL of 1-hexane thiol were added to the solution; and the mixture was stirred at room temperature for 4 hours. Water was then added to the reaction solution thus obtained, which was extracted with chloroform, and the resultant organic phase was washed with saturated saline, and dried with anhydrous sodium sulfate. After filtration, the solvent was removed by vacuum distillation. The resulting residue was purified by using silica gel column chromatography to yield 0.69 g of the Compound (III) as a colorless solid.

$^1$H-NMR (270 MHz, CDCl$_3$) δ 0.89 (3H, t, J=7.0 Hz), 1.30 (6H, complex), 1.55 (2H, dd, J=7.6, 14.9 Hz), 2.36 (2H, complex), 2.73 (5H, complex), 2.90 (2H, t, J=7.3 Hz); $^{13}$C-NMR (67.8 MHz, CDCl$_3$) 14.1, 22.5, 27.7, 28.5, 29.3, 29.4, 31.3, 37.1, 47.9, 166.8, 171.12, 171.15.

Similarly, the DTCM glutarimide C-12 represented by the Formula (IV) above was synthesized by using 1-dodecanethiol in place of 1-hexane thiol.

$^1$H-NMR (270 MHz, CDCl$_3$) δ 0.88 (3H, t, J=7.0 Hz), 1.27 (18H, complex), 1.55 (2H, dd, J=6.5, 13.2 Hz), 2.36 (2H, complex), 2.71 (5H, complex), 2.93 (2H, t, J=7.0 Hz); $^{13}$C-NMR (67.8 MHz, CDCl$_3$) 14.2, 22.7, 27.7, 28.9, 29.1, 29.3, 29.4, 29.5, 29.6, 29.7, 32.0, 37.2, 47.8, 166.8, 171.0.

(2) Evaluation of Toxicity of DTCM Glutarimide on Cells (I)

In this example, cytotoxicity of DTCM glutarimide on RAW264.7 cells was evaluated, based on cell survival rate and cell growth rate.

Figure 1:
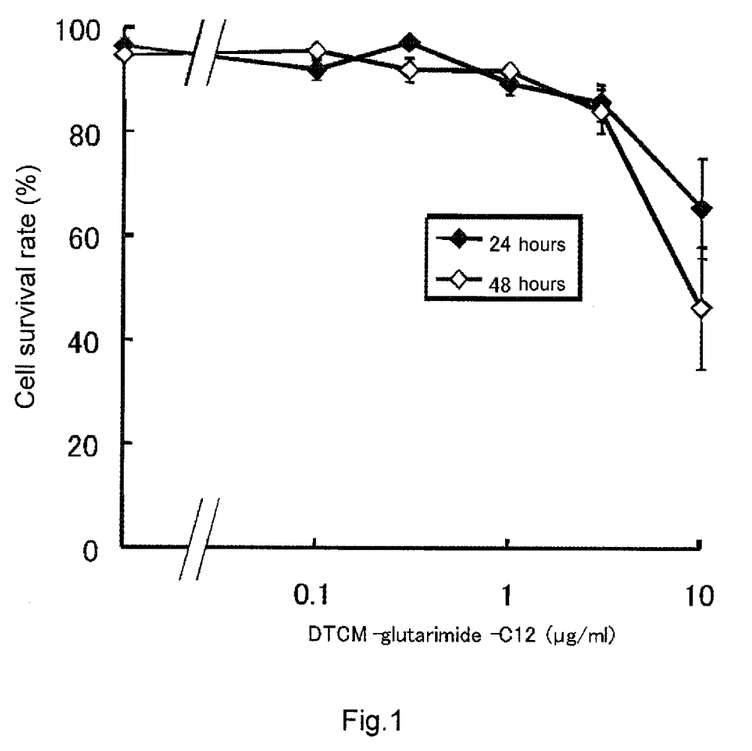
FIG. 1 is a graph showing survival rates of RAW264.7 cells after administration of DTCM glutarimide-C12 plotted against the concentration of the DTCM glutarimide in one example of the present invention.
Figure 2:
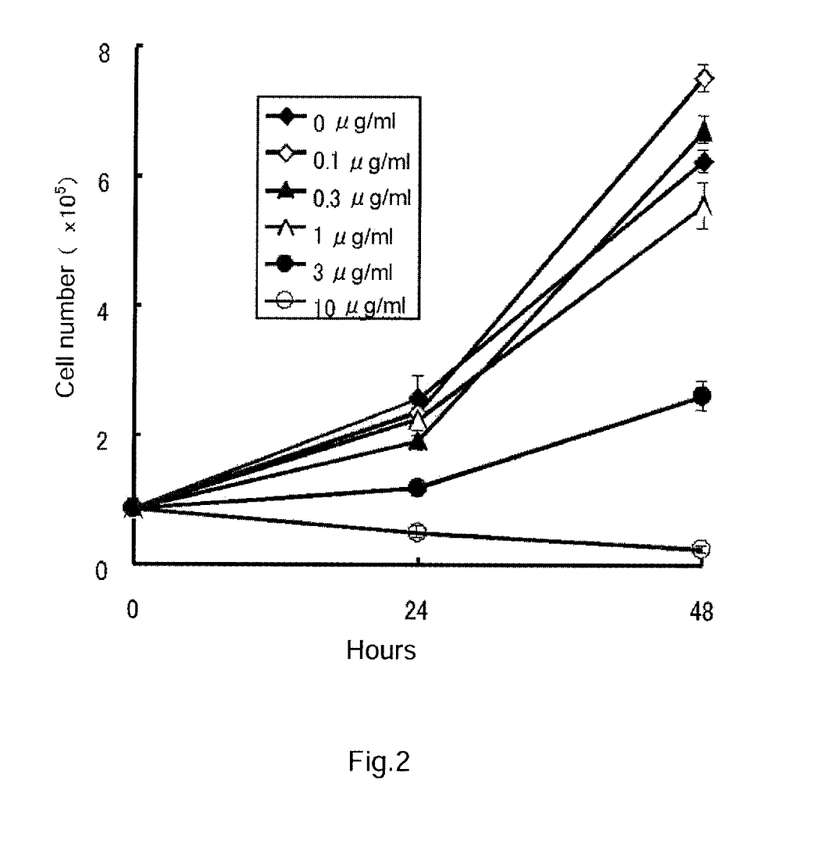
FIG. 2 is a graph showing growth rates of RAW264.7 cells after administration of DTCM glutarimide-C12 plotted against respective concentrations of the DTCM glutarimide in one example of the present invention.

The RAW264.7 cells were seeded on plastic dishes at $1\times10^4$ cells/ml in DMEM medium containing 10% FBS, to which DTCM glutarimide-C12 was added at the concentration of 0, 0.1, 0.3, 1.0, 3.0 or 10.0 μg/mL to the media. After 24 hours or 48 hours of culture, numbers of total cells were counted using hemacytometer, and numbers of living cells were counted using trypan blue dye exclusion assay. FIG. 1 shows the cell survival rates (living cell number/total cell number) at respective DTCM glutarimide concentrations, and FIG. 2 shows the total cell numbers plotted against respective culturing times.

As shown in FIG. 1, at the concentrations of DTCM glutarimide of up to 3.0 μg/mL, the cell survival rates did not mostly drop even after 48 hours, and thus no cell killing effect was detected. And as shown in FIG. 2, at the concentrations up to 1.0 μg/mL, the total cell number did not mostly drop even after 48 hours, and thus no suppression of cell growth was detected.

(3) Evaluation of Toxicity of DTCM Glutarimide on Cells (II)

In this example, the cytotoxicity of DTCM glutarimide on RAW264.7 cells was evaluated, based on the inhibition of synthesis of DNA, RNA and protein.

After RAW264.7 cells were cultured under the same conditions as in (2) with the media supplemented with DTCM glutarimide-C12 at concentrations (0, 0.1, 0.3, 1.0, 3.0 and 10.0 μg/mL) for 6 hours, $^3$H-labeled 0.1% thymidine, 0.1% uridine and 0.1% leucine were added to the media and the cells were further cultured for 1 hour. The cells were recovered and radioactivity of TCA-insoluble fractions was measured by using a liquid scintillation counter. The counts obtained at the DTCM glutarimide-C12 concentrations were normalized by setting to 100 the count obtained without addition of DTCM glutarimide-C12 in a control experiment and relatively plotted in the graph shown in FIG. 3.

Figure 3:
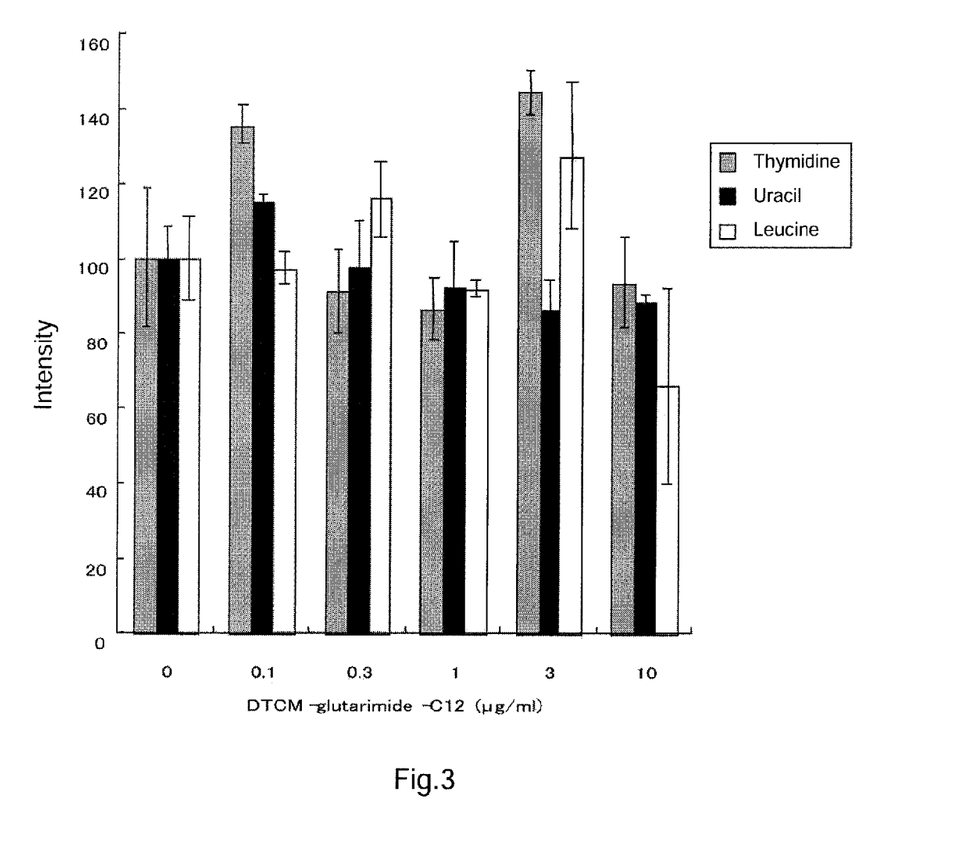
FIG. 3 is a graph showing inhibitions of synthesis of DNA, RNA and protein in RAW264.7 cells after administration of DTCM glutarimide-C12 plotted against the respective concentrations of the DTCM glutarimide in one example of the present invention.

As shown in FIG. 3, at the concentrations of DTCM glutarimide of up to 10.0 μg/mL, no significant inhibitory activity against the synthesis of any of DNA, RNA and protein was detected.

(4) Suppression of NO Production by Macrophage Activation by Use of DTCM Glutarimide In this example, it will be demonstrated that DTCM glutarimide suppresses NO production by activating macrophages.

After RAW264.7 cells were cultured under the same conditions as in (2) with the media supplemented with DTCM glutarimide-C12 at concentrations (0, 0.1, 0.3, 1.0 and 3.0 μg/mL) for 2 hours, 3.0 μg/mL of LPS was added to the media and the cells were further cultured for 20 hours. Then, NO production amounts were measured by Griess reaction and plotted against the respective DTCM glutarimide-C12 concentrations (the bar graph in FIG. 4).

Figure 4:
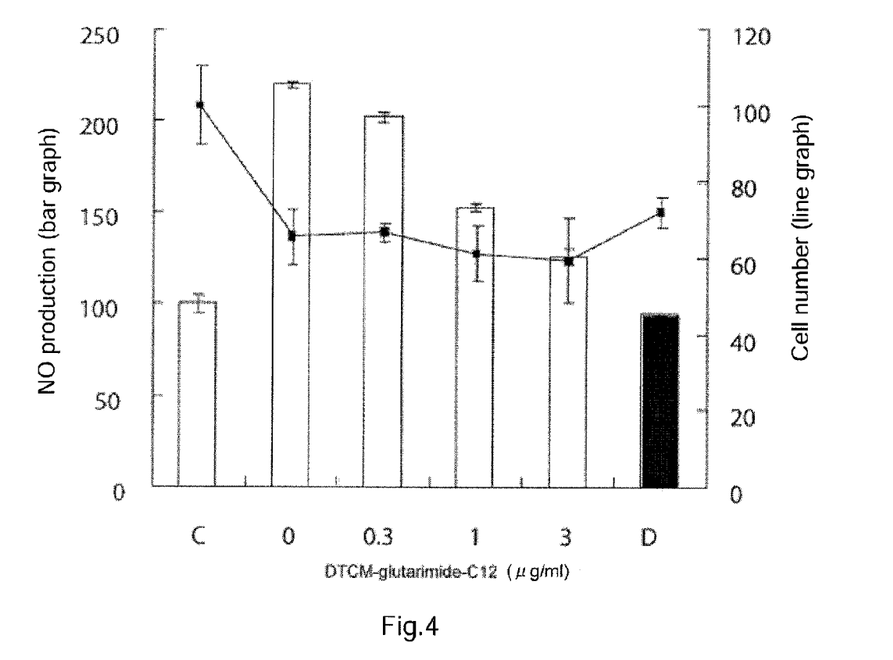
FIG. 4 is a graph showing that DTCM glutarimide-C12 suppresses NO production caused by macrophage activation in one example of the present invention.

As shown in FIG. 4, the RAW264.7 cells excessively produced NO at 20 hours after stimulation with LPS, but DTCM glutarimide-C12 significantly suppressed this NO production in a concentration-dependent manner. It should be noted that the cells which were not stimulated with LPS were used as a negative control without NO expression (hereinafter marked as "C" in the Figures), and the cells cultured in a medium supplemented with 10 μg/mL of (−)-DHMEQ instead of DTCM glutarimide-C12 were used as a positive control where NO expression is suppressed (hereinafter marked as "D" in the Figures).

At the same time, numbers of living cells were counted by MTT method to examine suppression of cell growth (the line graph in FIG. 4), and it was found that the total cell numbers were unchanged at all DTCM glutarimide-C12 concentrations, indicating that the addition of DTCM glutarimide-C12 did not affect the cell growth. Thus, the suppressive effect of DTCM glutarimide-C12 on NO production through the macrophage activation is not due to the suppression of cell growth.

Figure 5:
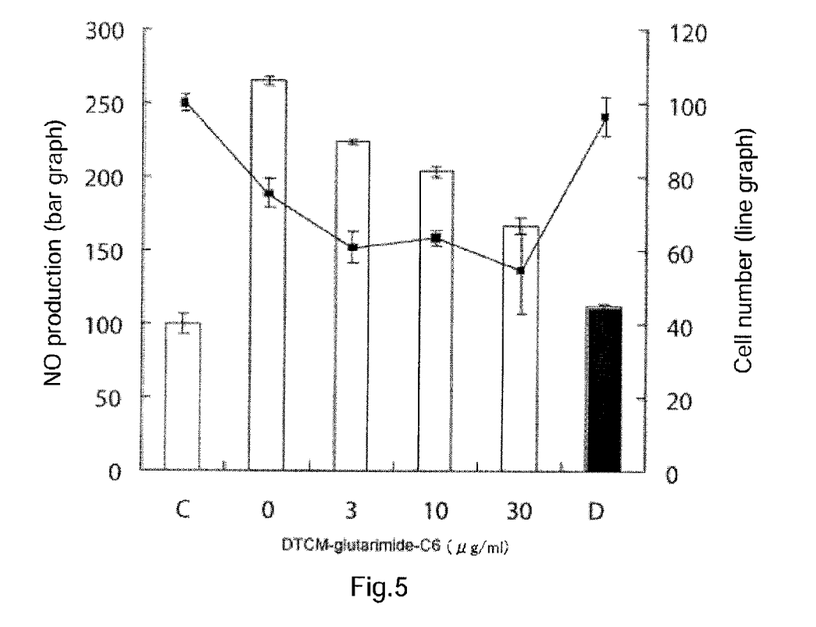
FIG. 5 is a graph showing that DTCM glutarimide-C6 suppresses NO production caused by macrophage activation in one example of the present invention.

A similar experiments were conducted using DTCM glutarimide-C16, which showed almost the same results (FIG. 5) as those using DTCM glutarimide-C12.

Further, based on the fact that once released into culture media, NO is rapidly metabolized into nitrite ($NO_2^-$), the nitrite in the culture supernatant was measured by Griess method and used as a marker for evaluating the NO scavenging activity of DTCM glutarimide-C12. A calibration curve was made, using sodium nitrite.

Sodium nitrite was dissolved in distilled water in 1.5 mL Eppendorf tubes to prepare sodium nitrite solutions at concentrations of 0.001, 0.01, 0.1 and 1.0 μg/mL, which were used to make the calibration curve. Then, 3.0 μg/mL of DTCM glutarimide-C12 were directly added to these sodium nitrite solutions. After leaving stand for 10 minutes, 100 μL of each of the solutions were put into a 96-well plate. 100 μL of Griess Reagent was added to the solutions and allowed to react for 10 minutes, and OD values at 570 nm wavelength were measured, using a microplate reader.

Figure 6:
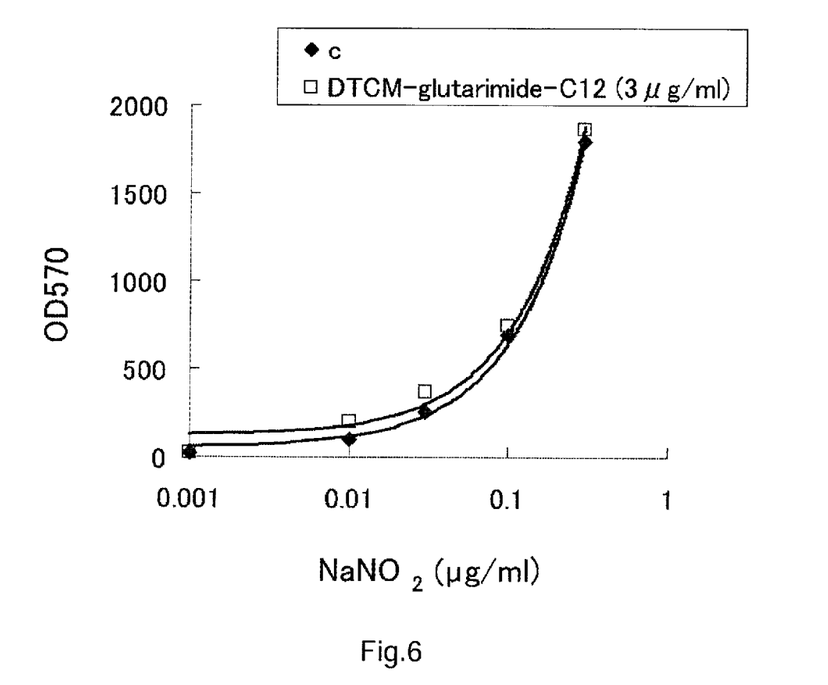
FIG. 6 is a graph showing that the suppressive effect of DTCM glutarimide-C12 on NO production caused by macrophage activation is not due to the NO scavenging activity of DTCM glutarimide-C12 in one example of the present invention.

As shown in FIG. 6, DTCM glutarimide-C12 did not exhibit NO scavenging activity.

Thus, the suppressive effect of DTCM glutarimide on the NO production through the macrophage activation is not due to the NO scavenging activity of DTCM glutarimide.

(5) Suppression of iNOS Expression in Macrophage Activation by Use of DTCM Glutarimide In this example, it will be demonstrated that DTCM glutarimide suppresses expression of iNOS gene in macrophage activation.

RAW264.7 cells were activated under the same conditions as in (4), the cells were recovered and proteins were extracted from the cells by a routine method. Western blotting was conducted, using an anti-iNOS antibody (Santa Cruz Biotechnology) and an anti-α-tubulin antibody (Sigma Aldrich Japan) at the dilution ratio of 1/3000. It should br noted that the cells which were not stimulated with LPS were used as a negative control without iNOS expression, and the cells cultured in a medium supplemented with 10 μg/mL of (−)-DHMEQ instead of DTCM glutarimide-C12 were used as a negative control where iNOS expression is suppressed.

Figure 7:
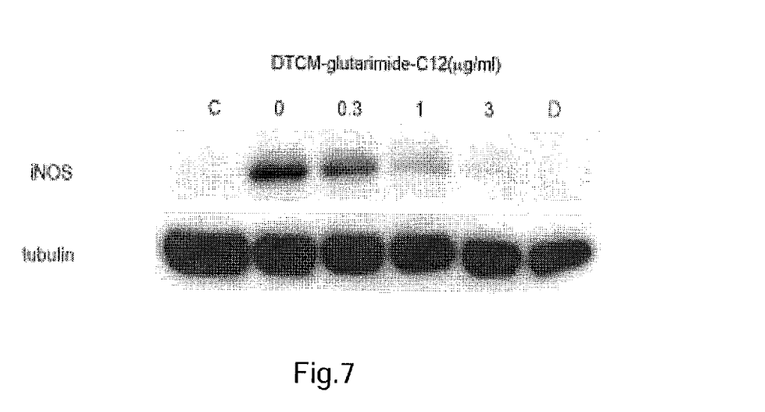
FIG. 7 is a graph showing that DTCM glutarimide-C12 suppresses the iNOS expression in the macrophage activation in one example of the present invention.

As shown in FIG. 7, the RAW264.7 cells came to express iNOS by stimulation with LPS, but DTCM glutarimide-C12 prominently suppressed this iNOS expression in a concentration-dependent manner.

Thus, DTCM glutarimide suppresses the expression of iNOS gene in the macrophage activation, and the extent of the suppression correlates with the concentration of DTCM glutarimide.

(6) Suppression of COX-2 Expression in Macrophage Activation by Use of DTCM Glutarimide In this example, it will be demonstrated that DTCM glutarimide suppresses expression of COX-2 gene in macrophage activation.

RAW264.7 cells were activated under the same conditions as in (4), the cells were recovered, proteins were extracted from the cells in a routine method, and Western blotting was conducted using an anti-COX-2 antibody (BD Bioscience) and an anti-α-tubulin antibody (Sigma Aldrich Japan) at the dilution ratio of 1/3000. It should br noted that the cells which were not stimulated by LPS were used as a negative control without COX-2 expression, and, the cells cultured in a medium supplemented with 10 μg/mL of (−)-DHMEQ instead of DTCM glutarimide-C12 were used as a positive control where COX-2 expression is suppressed.

Figure 8:
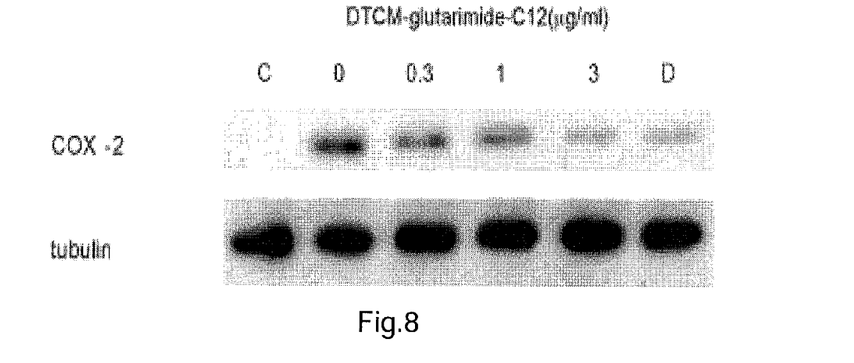
FIG. 8 is a graph showing that DTCM glutarimide-C12 suppresses the expression of COX-2 gene in the macrophage activation in one example of the present invention.

As shown in FIG. 8, the RAW264.7 cells came to express COX-2 by stimulation with LPS, but DTCM glutarimide-C12 prominently suppressed this COX-2 expression in a concentration-dependent manner.

Thus, DTCM glutarimide suppresses the expression of COX-2 gene in the macrophage activation, and the strength of the suppression correlates with the concentration of DTCM glutarimide.

(7) DTCM Glutarimide does not Affect IL-6 Production by Macrophage Activation Macrophages activated by an inflammatory stimulation produce inflammatory cytokines such as IL-6 and TNF-α. In this example, it will be demonstrated that DTCM glutarimide does not affect the IL-6 production by the macrophage activation.

RAW264.7 cells were activated under the same conditions as in (4), the cells were recovered, proteins were extracted from the cells by a routine method. An ELISA was conducted using 96-well polystyrene microplates onto which the anti-IL-6 antibody had been immobilized. It should be noted that the cells which were not stimulated with LPS were used as a negative control without the IL-6 production, and the cells cultured in a medium supplemented with 10 μg/mL of (−)-DHMEQ instead of DTCM glutarimide-C12 were used as a positive control where the IL-6 production is suppressed. The detected concentrations of IL-6 per $10^6$ cells were plotted in FIG. 9.

Figure 9:
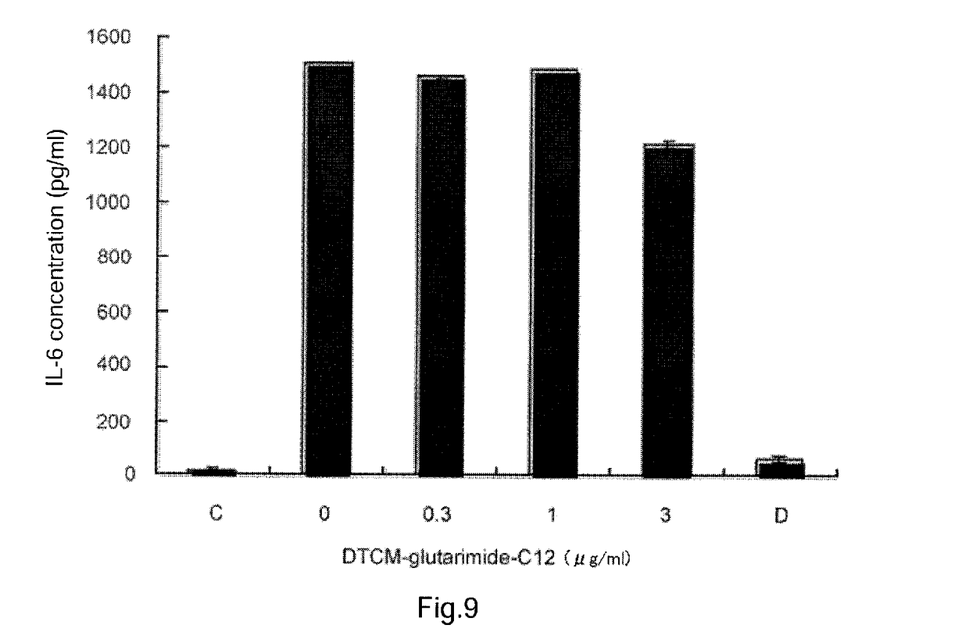
FIG. 9 is a graph showing that DTCM glutarimide-C12 does not affect the IL-6 production caused by the macrophage activation in one example of the present invention.

As shown in FIG. 9, the RAW264.7 cells came to express IL-6 by stimulation with LPS, and the DTCM glutarimide-C12 did not affect this IL-6 production at the concentrations below 3.0 μg/mL.

Thus, DTCM glutarimide does not inhibit the IL-6 expression in the macrophage activation at the concentrations where no cytotoxicity is exhibited.

(8) DTCM Glutarimide does not Affect NF-κB Activation in Macrophage Activation NF-κB, which participates in signal transductions from cytoplasm to nucleus, is known as a transcription factor involved in induction of expression of various genes by stimulations in immunity and inflammation responses. A stimulation by LPS, which activates macrophages, can activate NF-κB via TLR4 in RAW264.7 cells. NF-κB usually remains in cytoplasm in an inactivated state forming a complex with an inhibitory protein IκB, but once stimulated by LPS etc., IκB-α will be phosphorylated and then ubiquitinated and degraded by proteasome. Since the promoter region of IκB-α has an NF-κB binding site, IκB-α will be re-induced by the NF-κB activation. Thus, NF-κB plays an important roll in regulations after the macrophage activation. In this example, it will be demonstrated that DTCM glutarimide does not affect the NF-κB activation in the macrophage activation.

First, under the same conditions as in (2), RAW264.7 cells were cultured for 2 hours with the culture media with and without supplementation of 3.0 μg/mL of DTCM glutarimide-C12, and following addition of 3.0 μg/mL of LPS, the cells were further cultured for 0, 5, 15, 30 or 60 minutes. The cells were recovered from each, proteins were extracted from the cells by a routine method. Western blotting was conducted to the extract using an anti-IκB-α antibody (Santa Cruz Biotechnology) at the dilution ratio of 1/500 and an anti-α-tubulin antibody (Sigma Aldrich Japan) at the dilution ratio of 1/3000.

Figure 10:
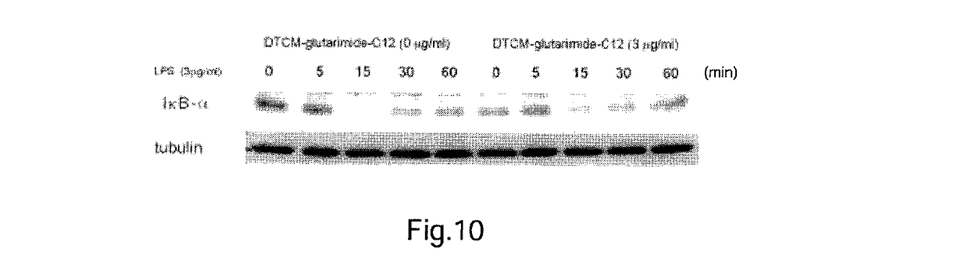
FIG. 10 is a graph showing, based on degradation and reinduction of IκB-α, that DTCM glutarimide-C12 does not affect NF-κB activation in the macrophage activation in one example of the present invention.

As shown in FIG. 10, in the cells not treated by DTCM glutarimide-C12, IκB-α degradation occurred at 15 minutes after the stimulation with LPS, and the IκB-α reinduction took place after 30 minutes. Even when the cells have been pretreated by DTCM glutarimide-C12, the degradation and reinduction of IκB-α were not affected at the concentrations where no cytotoxicity was exhibited.

Next, under the same conditions as in (2) above, RAW264.7 cells were cultured with the media supplemented with DTCM glutarimide-C12 at concentrations (0, 0.1, 0.3, 1.0 and 3.0 μg/mL) for 2 hours, to which 3.0 μg/mL of LPS was added, and the cells were further cultured for 30 minutes. Then, nuclear extracts were prepared by a routine method, and a gel shift assay was conducted with using 3 μL of a $^{32}$P-labeled probe.

The probe was prepared as follows. First, 4 μL of 1.75 μmol/mL oligonucleotide (Promega Inc.) (5'-ATGT-GAGGGGACTTTCCCAGGC-3'; SEQ ID N0.1), 4 μL of 10×T4 PNK buffer (Takara) and 10 μL of nucleotide free water were mixed, to which 2 μL of [γ-$^{32}$P]-ATP (Amarsham Corp.) was added, and incubated at 37° C. for 10 minutes. The reaction was then terminated by addition of 80 μL of TE buffer (10 mM Tris-HCl:1 mM EDTA=1:1). 100 μL of the reaction solution was loaded onto a Nick Column (Amersham Corp.) which had been prepared by removing the filled TE buffer and washing with distilled water, 400 μL of distilled water was loaded, and the eluate from the column was recovered in a 1.5 mL Eppendorf tube. Additional 400 μL of distilled water was loaded, and the fraction eluted again from the column was recovered in the 1.5 mL Eppendorf tube. The elute thus obtained was used as the labeled DNA probe.

It should be noted that the cells which were not stimulated by LPS were used as a negative control without NF-κB activation, and the cells cultured in a medium supplemented with 10 μg/mL of (−)-DHMEQ instead of DTCM glutarimide-C12 were used as a positive control where the activity of NF-κB is suppressed. The signal of the probe bound with NF-κB was identified on the basis of extinction by DHMEQ and occurrence of super-shift by an anti-p65 antibody (Santa Cruz Biotechnology).

Figure 11:
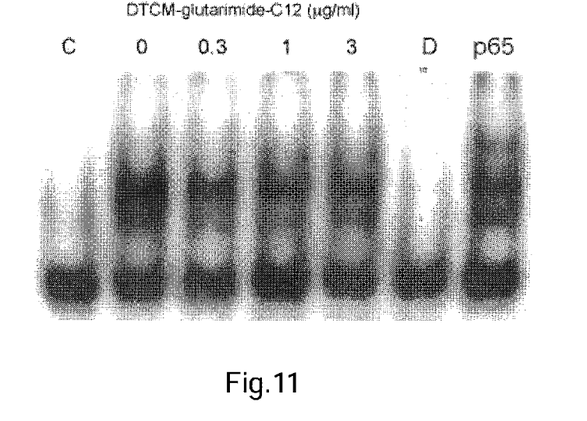
FIG. 11 is a graph showing, based on the DNA binding capability of NF-κB, that DTCM glutarimide-C12 does not affect NF-κB activation in the macrophage activation in one example of the present invention.

As shown in FIG. 11, NF-κB activation was observed upon the stimulation by LPS, and the pretreatment by DTCM glutarimide-C12 did not suppress the DNA binding ability of NF-κB at the concentrations below 3.0 μg/mL.

Thus, DTCM glutarimide does not inhibit the NF-κB activation in the macrophage activation at the concentrations where no cytotoxicity is exhibited.

(9) DTCM Glutarimide does not Affect MAPK Activation by Macrophage Activation It has been known that the NO production induced by macrophage activation involves activation of not only NF-κB but also MAPKs including ERK1/2, JNK and p38. It was also reported that the activation of MAPKs including ERK1/2, JNK and p38 was essential for expression of genes for inflammatory cytokines. In this example, though, it will be demonstrated that TCM glutarimide does not affect phosphorylation of p38, ERK and JNK in the macrophage activation.

First, protein extracts were similarly prepared as in (8), and used in a Western blotting with each of an anti-phosphorylated p38 antibody (Cell Signaling Technology), an anti-p38 antibody (Santa Cruz Biotechnology), an anti-phosphorylated ERK antibody (Cell Signaling Technology), an anti-ERK antibody (Santa Cruz Biotechnology), an anti-phosphorylated JNK antibody (Cell Signaling Technology) and an anti-JNK antibody (Santa Cruz Biotechnology) at the dilution ratio of 500:1, and an anti-α-tubulin antibody (Sigma Aldrich Japan) at the dilution ratio of 300:1.

Figure 12:
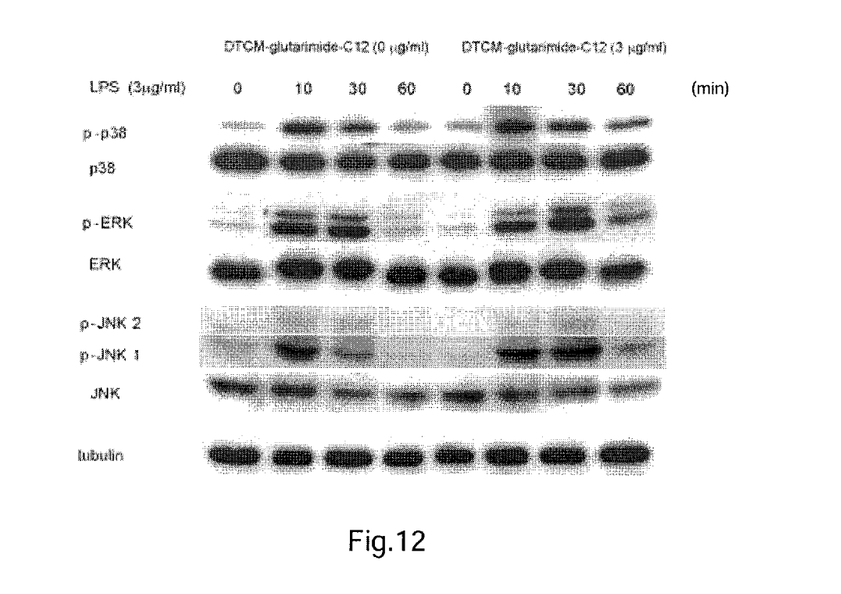
FIG. 12 is a graph showing that DTCM glutarimide-C12 does not affect MAPK activation caused by the macrophage activation in one example of the present invention.

As shown in FIG. 12, in the cells not treated by DTCM glutarimide-C12, p38 was activated 10 minutes after the cells were stimulated with LPS, and the activation was decreased 60 minutes after. In the cells pretreated by DTCM glutarimide-C12, this pattern of p38 activation was not different.

Similarly, ERK was activated in the cells not treated by DTCM glutarimide-C12 10 minutes after the cells were stimulated with LPS, and the activation was decreased 60 minutes after. In the cells pretreated by DTCM glutarimide-C12, this pattern of ERK activation was not different.

Thus, DTCM glutarimide does not affect the MAPK activation in the macrophage activation at the concentrations where no cytotoxicity is exhibited.

(10) Evaluation of Toxicity of DTCM Glutarimide on Murine Bone Marrow-Derived Macrophages In this example, the cytotoxicity of DTCM glutarimide on primary macrophages derived from a murine bone marrow was evaluated based on the survival rate of the cells.

An 8 week-old ICR mouse (male, purchased from Charles River) sacrificed by cervical dislocation was dissected under sterile conditions to isolate femora and cubiti from both legs. Medullary cavities were washed with α-MEM several times using a 21G needle attached to a 1 mL syringe. The fluid (α-MEM) after washing was filtrated through a nylon mesh (330 mesh) to remove unnecessary cells, and myelocytes were isolated. The myelocyte suspension in α-MEM thus obtained was diluted to 1.25 to $3.75\times10^6$ cell/mL. To 80 mL of the myelocyte suspension, 80 μL of hM-CSF (Wako Pure Chemical) at 10 μg/mL prepared with PBS containing 0.1% BSA was added (final concentration 10 ng/mL). The cells thus prepared were seeded onto 24-well plates (Corning Inc.) by 500 μL to 1 mL per well, and cultured at 37° C. under 5% $CO_2$ for 2 days. Then, unattached cells were washed away with α-MEM, fresh α-MEM containing 10 ng/mL of hM-CSF was added, and the attached cells thus obtained were used as the murine bone marrow-derived macrophages.

The murine bone marrow-derived macrophages thus prepared were seeded onto 24-well plates (Corning Inc.) by 1 mL each (1.25 to $3.75\times10^6$ cell/mL). To each of the wells, DTCM glutarimide-C12 at respective concentrations of 1.0, 3.0, 10.0 and 30.0 μg/mL was added, and all the experimental groups were cultured at 37° C. under 5% $CO_2$. The control group was cultured under the same condition but without addition of DTCM glutarimide-C12.

==Measurement of Cell Survival Rate by Trypan Blue Staining (Trypan Blue Dye Exclusion Assay)==

The cells in the experimental groups were detached using a cell scraper and dissolved in α-MEM at 24 hours, 48 hours and 72 hours after the addition of DTCM glutarimide-C12. Then 1 mL of the cell suspensions were recovered in fresh Eppendorf tubes. Similarly in the control group, cell suspensions were recovered at 24 hours, 48 hours and 72 hours after the start of culture. The cell suspensions were centrifuged at 3500 rpm for 5 min to sediment the cells. For the experimental groups, the supernatants were discarded. For the control group, the supernatant was recovered. Then, 80 μL of the supernatant recovered from the control group and 20 μL of trypan blue staining solution which had been prepared by dissolving 4 mg of trypan blue in 1 mL of 9 mg/mL NaCl were added to the cell pellets in experimental groups and the control groups and resuspended, thereby staining dead cells in blue by trypan blue. 10 μL of the cell suspensions was put onto a hemacytometer (Erma Inc.) and total cells and dead cells were counted under a microscope at 100× magnification. In hemacytometric counting, approximately 100 cells were counted per one visual field, and the cell survival rates obtained in four visual fields were averaged. The cell survival rate (%) was calculated according to the following formula.

Survival rate (%)=(Total cell number−Dead cell number)/Total cell number×100

Figure 13:
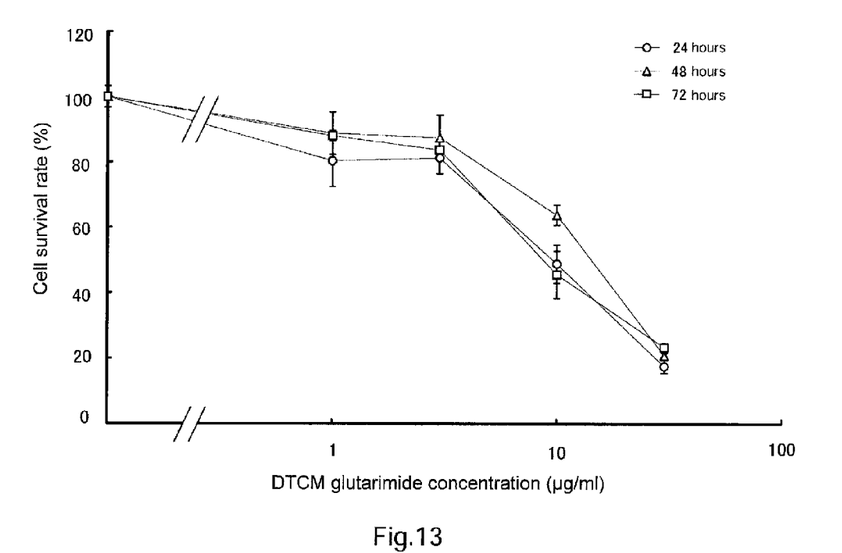
FIG. 13 is a graph showing that DTCM glutarimide-C12 at the concentrations below 3.0 μL does not exhibit toxicity on murine bone marrow-derived macrophages in one example of the present invention.

As shown in FIG. 13, in the groups of 3.0 μL DTCM glutarimide-C12, the survival rates of the murine myelocyte-derived macrophages were more than 80% regardless of the culture time. On the other hand, in the groups of 10.0 and 30.0 μL DTCM glutarimide-C12, the survival rates of the murine myelocyte-derived macrophages were reduced regardless of the culture time.

This result indicates that DTCM glutarimide-C12 at the concentrations up to 3.0 μL does not exhibit toxicity on the murine myelocyte-derived macrophages. Thus, the concentration of DTCM glutarimide-C12 in the following Examples where murine bone marrow-derived macrophages were used was set to 3.0 μg/mL or less.

(11) Suppression of Osteoclast Differentiation of Murine Bone Marrow-Derived Macrophages by DTCM Glutarimide In this example, it will be demonstrated that DTCM glutarimide suppresses differentiation of murine bone marrow-derived macrophages into osteoclasts.

The primary murine bone marrow-derived macrophages prepared in Example (10) were plated onto 24-well plates (Corning Inc.) by 500 μL each (1.25 to $3.75\times10^6$ cell/mL). Then 5 μL of DTCM glutarimide-C12 was added to each of the wells to the final concentrations of 0, 0.3, 1.0 and 3.0 μg/mL. All the experimental groups of plates were cultured at 37° C. under 5% $CO_2$ for 2 hours. hRANKL (Wako Pure Chemical) at 10 μg/mL prepared in PBS containing 0.1% BSA was then added by 5 μL each (final concentration 100 ng/mL), and culture was continued. RANKL has been known as a factor to induce osteoclasts differentiation of macrophages etc. (Kobayashi et al. Crit. Rev Eukaryot Gene Expr.

19(1), 61-72, 2009). The control group of plates was cultured under the same condition but without RANKL and DTCM glutarimide.

After 5 days of culture, the media were removed, and the cells were washed by PBS. 250 μL each of 3.5% paraformaldehyde was added to the wells to fix the cells for 5 minutes, and the fixative was washed away with PBS. Then, 250 μL of acetone:ethanol (1:1 v/v) was added and left stand for 30 seconds for delipidation. After washing with PBS, 500 μL of a staining solution for tartrate-resistant acid phosphatase (TRAP) (0.01% naphthol AS-MX phosphate-0.05% Fast Red Violet LB salt in TRAP buffer (50 mM L-sodium tartrate, 90 mM sodium acetate trihydrate)) was added per well and the plates were incubated at room temperature for 5 to 20 minutes, and upon confirmation of staining, the staining solution was removed to stop the reaction. Following an addition of 250 μL of PBS, the plates were observed under a microscope and the number of mature osteoclasts was counted in the entire visual field by regarding TRAP-positive cell having three or more fused nuclei as the mature osteoclast as it is known to be TRAP-positive.

Figure 14:
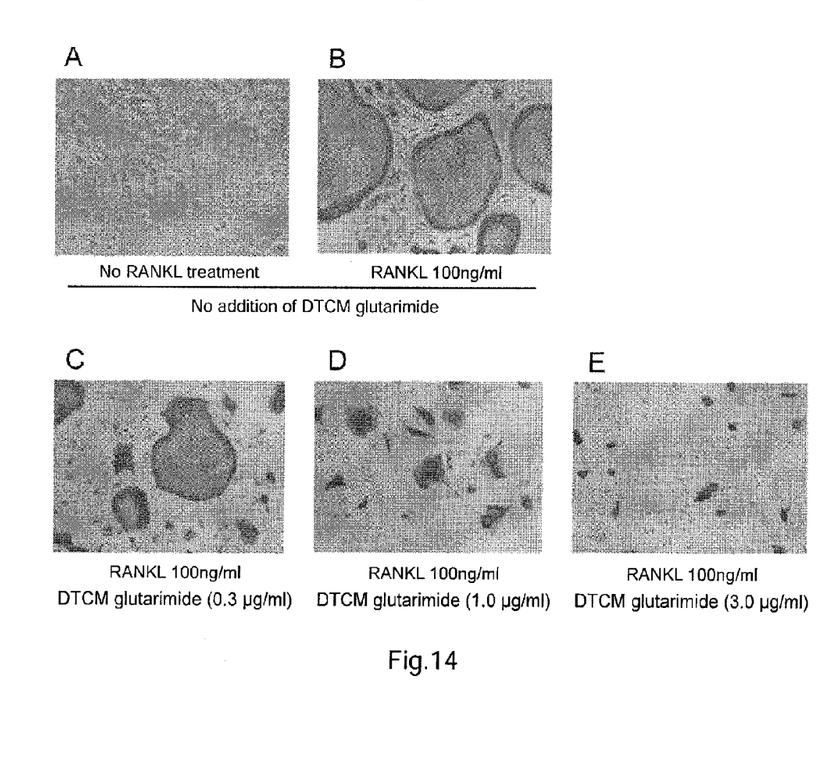
FIG. 14 is a set of micrographs showing the effects of RANKL treatment and DTCM glutarimide-C12 treatment on the induction of differentiation of murine bone marrow-derived macrophages into osteoclasts in one example of the present invention.
Figure 15:
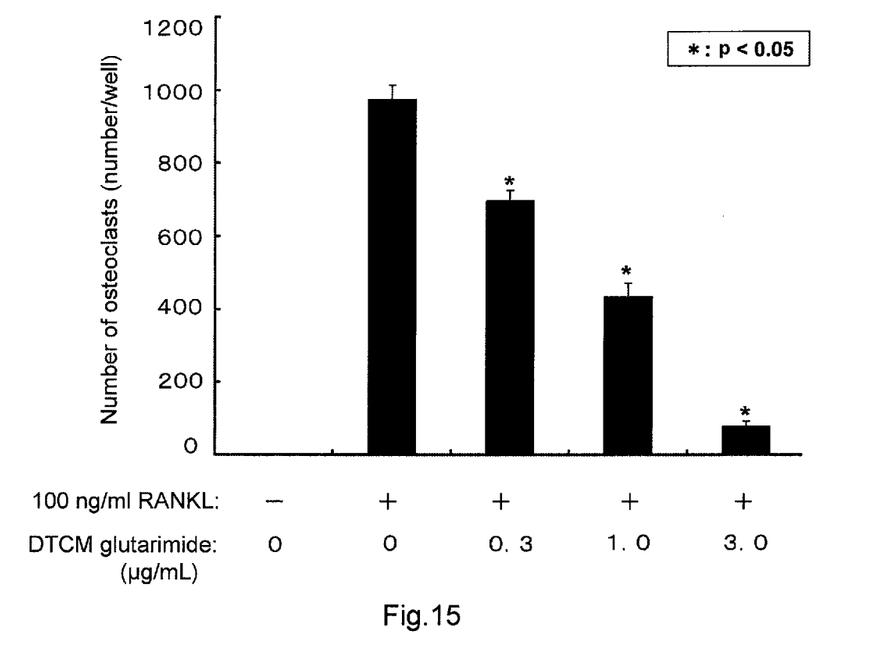
FIG. 15 is a graph showing the numbers of osteoclasts differentiated from murine bone marrow-derived macrophages after treatment with RANKL or DTCM glutarimide-C12 in one example of the present invention.

As shown in FIG. 14 and FIG. 15, no osteoclast was observed in the group without the addition of RANKL (FIG. 14A), whereas osteoclast differentiation was induced in the group with the addition of RANKL (FIG. 14B). Further, when DTCM glutarimide-C12 was added, the number of osteoclasts was significantly reduced (FIG. 14C to E, FIG. 15).

This result indicates that DTCM glutarimide suppresses the osteoclast differentiation of macrophages. Accordingly, DTCM glutarimide is useful for treatment of various diseases involving osteoclasis by the osteoclasts.

the suspensions were counted by Coulter Counter (Beckman Coulter Inc.) to evaluate cell growth.

Figure 16:
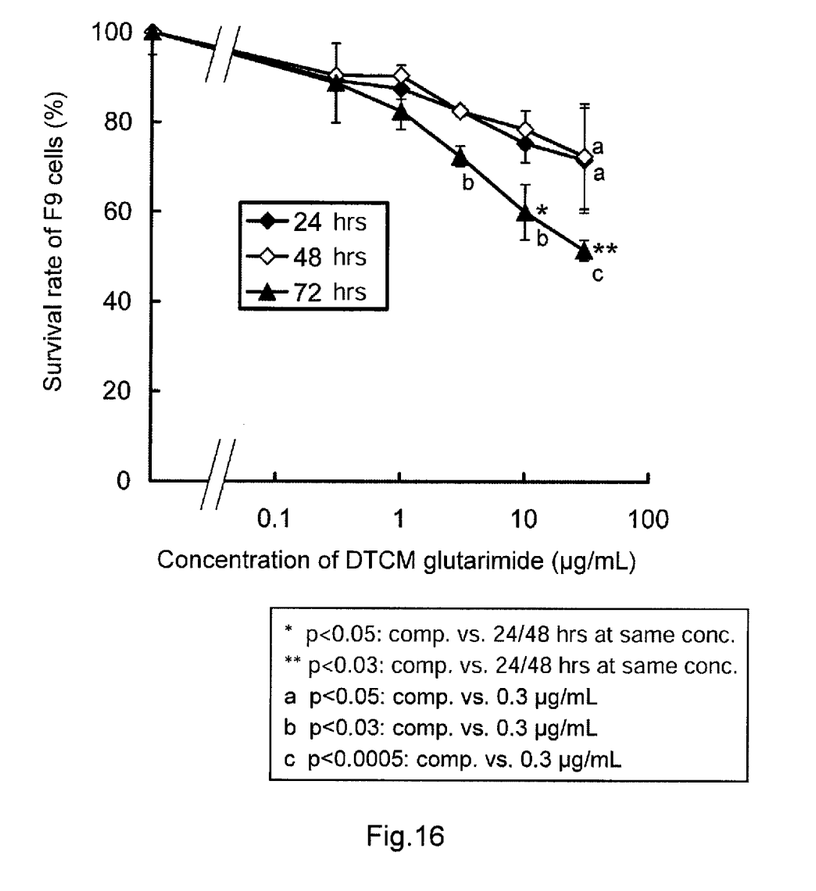
FIG. 16 is a graph showing the survival rates of F9 cells after treatment with DTCM glutarimide-C12 in one example of the present invention.

As shown in FIG. 16, the cell survival rates of F9 cells were significantly reduced in the groups with any culturing time depending on the concentration of DTCM glutarimide-C12 (judged by t test). In the cases where the DTCM glutarimide-C12 concentration was 10 or 30 μg/mL, the group of 72-hour culturing had significantly reduced cell survival rate in comparison with the groups of 24-hour and 48-hour culturing.

Figure 17:
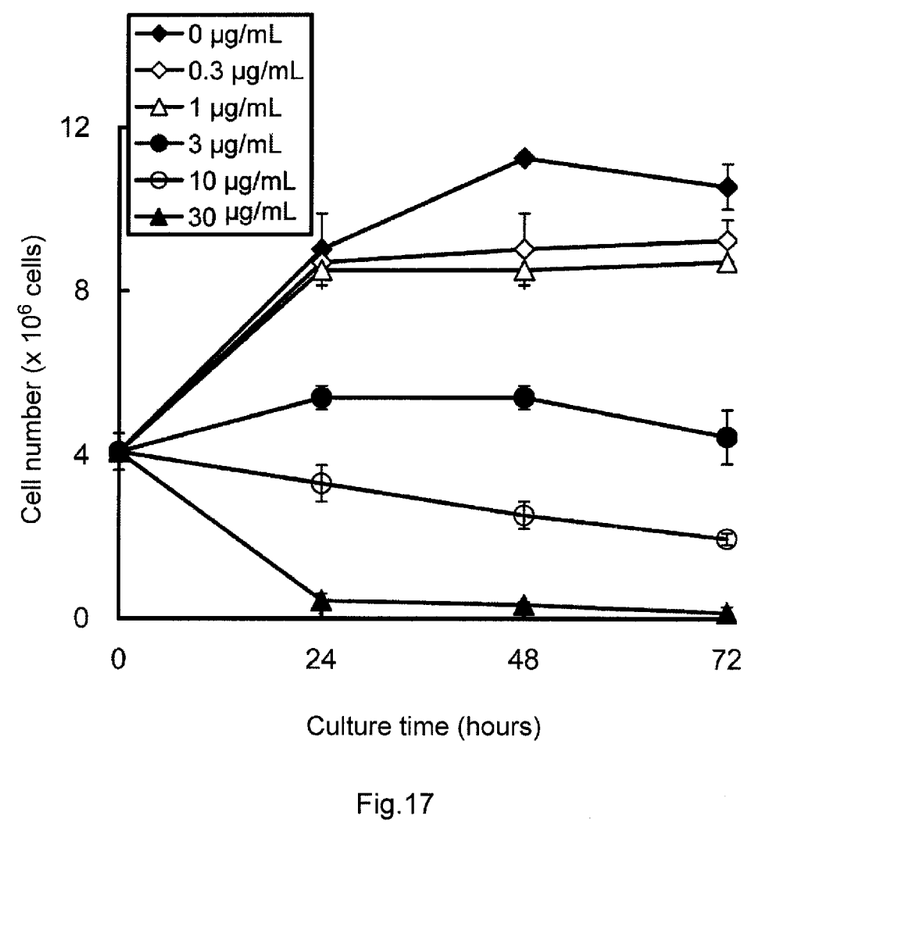
FIG. 17 is a graph showing the growth of F9 cells after treatment with DTCM glutarimide-C12 in one example of the present invention.

Also, as shown in FIG. 17, the cell growth was suppressed in the groups cultured with the addition of DTCM glutarimide-C12, in comparison with the group without the addition of DTCM glutarimide-C12. The more effective suppression of the cell growth was exhibited with the higher concentration of DTCM glutarimide-C12 and with the longer culturing time after the addition of DTCM glutarimide-C12.

This result indicates that DTCM glutarimide has the effect to reduce the survival rate of tumor cells and the effect to suppress their growth. Accordingly, DTCM glutarimide is useful for treatment of various kinds of tumors.

INDUSTRIAL APPLICABILITY

According to the present invention, a pharmaceutical composition to inhibit expression of iNOS and COX-2 without inhibiting NF-κB can be provided.

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: probe for gelshift

<400> SEQUENCE: 1
atgtgagggg actttcccag gc                                              22
```

(12) Reduction of Survival Rate and Suppression of Growth of Cancer Cells by DTCM Glutarimide In this example, it will be demonstrated that DTCM glutarimide has an effect to reduce the survival rate of cancer cells and to suppress their growth.

F9 cells derived from murine embryonic tumor cells (purchased from RIKEN Tsukuba Institute BioResource Center, Cell Engineering Division) were plated onto plastic dishes at $1 \times 10^4$ cell/mL in DMEM medium containing 15% FBS. DTCM glutarimide-C12 was then added at the concentration of 0, 0.1, 0.3, 1.0, 3.0, 10.0 or 30.0 μg/mL in the culture media, and were cultured for 24, 48 or 72 hours. By following the same method as described in "Measurement of Cell Survival Rate by Trypan Blue Staining" in Example (10), the survival rates of cells were measured. Also, suspensions of the cultured cells were similarly prepared and the numbers of cells in

The invention claimed is:

1. A method for treating a disease mediated by iNOS or COX-2, comprising the step of administering to a patient suffering from the disease an effective amount of the compound of Formula (I):

(I)

wherein n is an integer of 1 to 24, and
wherein the disease is osteoarthritis.

* * * * *

UNITED STATES PATENT AND TRADEMARK OFFICE
CERTIFICATE OF CORRECTION

PATENT NO. : 8,524,747 B2
APPLICATION NO. : 13/000442
DATED : September 3, 2013
INVENTOR(S) : Umezawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 295 days.

Signed and Sealed this
Twenty-third Day of May, 2017

Michelle K. Lee
*Director of the United States Patent and Trademark Office*